US012799472B2

(12) United States Patent
Zanphorlin Murakami et al.

(10) Patent No.: US 12,799,472 B2
(45) Date of Patent: Nov. 17, 2026

(54) CHIMERIC ENZYME AND METHOD FOR PRODUCING TERMINAL ALKENES

(71) Applicant: CNPEM—CENTRO NACIONAL DE PESQUISA EM ENERGIA E MATERIAIS, Campinas (BR)

(72) Inventors: Leticia Maria Zanphorlin Murakami, Campinas (BR); Wesley Cardoso Generoso, Campinas (BR); Gabriela Felix Persinoti, Campinas (BR)

(73) Assignee: CNPEM—CENTRO NACIONAL DE PESQUISA EM ENERGIA E MATERIAIS, Campinas (BR)

( * ) Notice: Subject to any disclaimer, the term of this patent is extended or adjusted under 35 U.S.C. 154(b) by 219 days.

(21) Appl. No.: 18/717,196

(22) PCT Filed: Dec. 6, 2022

(86) PCT No.: PCT/BR2022/050482
§ 371 (c)(1),
(2) Date: Jun. 6, 2024

(87) PCT Pub. No.: WO2023/102629
PCT Pub. Date: Jun. 15, 2023

(65) Prior Publication Data

US 2025/0115892 A1 Apr. 10, 2025

(30) Foreign Application Priority Data

Dec. 6, 2021 (BR) .......................... 1020210246723

(51) Int. Cl.
*C12N 9/88* (2006.01)
*C12N 9/04* (2006.01)
*C12P 5/02* (2006.01)

(52) U.S. Cl.
CPC ............. *C12N 9/88* (2013.01); *C12N 9/0006* (2013.01); *C12P 5/026* (2013.01); *C12Y 101/03041* (2013.01)

(58) Field of Classification Search
CPC ........ C12N 9/88; C12N 9/0006; C12N 15/52; C12N 15/62; C12P 5/026
See application file for complete search history.

(56) References Cited

U.S. PATENT DOCUMENTS

| | | | |
|---|---|---|---|
| 9,885,060 B2 | 2/2018 | Dennig | |
| 11,060,099 B2 | 7/2021 | Greenfield | |
| 11,236,367 B2 | 2/2022 | Beisson | |
| 2025/0115892 A1* | 4/2025 | Zanphorlin Murakami ................ | C12N 9/88 |

FOREIGN PATENT DOCUMENTS

| | | |
|---|---|---|
| CN | 107201356 | 9/2017 |
| CN | 112111477 | 12/2020 |
| EP | 1940348 | 7/2008 |

OTHER PUBLICATIONS

Sarah Matthews et al: "Production of alkenes and novel secondary products by P450 OleTJE using novel H202-generating fusion protein systems", Febs Letters, Elsevier, Amsterdam, NL, vol. 591, No. 5, Feb. 21, 2017 (Feb. 21, 2017), pp. 737-750, XP071256176, ISSN: 0014-5793, DOI: 10.1002/1873-3468.12581.

Zhang Libo et al: "Enhanced P450 fatty acid decarboxylase catalysis by glucose oxidase coupling and co- assembly for biofuel generation", Bioresource Technology, Elsevier, Amsterdam, NL, vol. 311, May 15, 2020 (May 15, 2020), XP086155837, ISSN: 0960-8524, [retrieved on May 15, 2020], DOI: 10.1016/J.BIORTECH. 2020. 123538.

* cited by examiner

*Primary Examiner* — Tekchand Saidha
(74) *Attorney, Agent, or Firm* — FisherBroyles, LLP; Jason P. Mueller

(57) ABSTRACT

The present invention refers to a chimeric enzyme constructed for the production of terminal alkenes from fatty acids, so that the cofactor necessary for the reaction is produced in situ from industrial waste, favoring the circular economy. Furthermore, the present invention deals with the process of producing terminal alkenes using said chimeric enzyme. This invention belongs to the field of industrial biotechnology and finds application in the biofuels and renewable chemicals industry.

15 Claims, 1 Drawing Sheet

Specification includes a Sequence Listing.

SEQUENCE LISTING

```
Sequence total quantity: 8
SEQ ID NO: 1          moltype = AA  length = 429
FEATURE               Location/Qualifiers
source                1..429
                      mol_type = protein
                      organism = Rothia nasimurium
SEQUENCE: 1
MNIAPVKNLL NDQLPNFIKQ GYLFMSHQRR KAGVPADSNC PVTFPVLGGR ATLIRGEEAV  60
DFFYDESKIS RNGAMPTAIQ GPLFGDGAVH TLDGQAHKVR KSAMAAMAYD DERVEAFRGF  120
VEEEMKALIE RWKTNPGNIY DDVAVAYGRA AFRWAGVPAS DRELNKRATQ MSHLLDTFGE  180
VKQNVLSWMD RRKLDAWAED LIKKVRSGEL TVDPDSVVRH MADLRDEKGE LVTAKLAGIE  240
LQNLTRPTVA VSRFAAFAAV AMVENPEWAA KVKNAVEDAD GRLVNIPEAV AFAQETRRKY  300
PFVPMLPAMV KEDTELSGCP IQKGQRVFLD VLGTNNSPQL WNNPGEFNPQ RFLDTPDYES  360
IKGFIPQGGG DVLTGHRCPG EKIAVAALSS TVAALSADNV TISQETEDTT FSMTQLLTRP  420
RTGVRVTVS                                                          429

SEQ ID NO: 2          moltype = AA  length = 418
FEATURE               Location/Qualifiers
source                1..418
                      mol_type = protein
                      organism = Streptomyces sp.
SEQUENCE: 2
MSDITVTNWA GNITYTAKEL LRPHSLDALR ALVADSARVR VLGSGHSFNE IAEPGDGGVL  60
LSLAGLPSVV DVDTAARTVR VGGGVRYAEL ARVVHARGLA LPNMASLPHI SVAGSVATGT  120
HGSGVGNGSL ASVVREVELV TADGSTVVIA RGDERFGGAV TSLGALGVVT SLTLDLEPAY  180
EMEQHVFTEL PLAGLDPATF ETVMAAAYSV SLFTDWRAPG FRQVWLKRRT DRPLDGFPYA  240
APAAEKMHPV PGMPAVNCTE QFGVPGPWHE RLPHFRAEFT PSSGAELQSE YLMPREHALA  300
ALHAMDAIRE TLAPVLQTCE IRTVAADAQW LSPAYGRDTV AAHFTWVEDT AAVLPVVRRL  360
EEALVPFAAR PHWGKVFTVP AGELRALYPR LADFGALAGA LDPAGKFTNA FVRGVLAG    418

SEQ ID NO: 3          moltype = AA  length = 11
FEATURE               Location/Qualifiers
source                1..11
                      mol_type = protein
                      organism = unidentified
SEQUENCE: 3
HSSGLVPRGS H                                                       11

SEQ ID NO: 4          moltype = AA  length = 13
FEATURE               Location/Qualifiers
source                1..13
                      mol_type = protein
```

-continued

```
                          organism = unidentified
SEQUENCE: 4
DASAREATAK GSH                                                    13

SEQ ID NO: 5              moltype = AA  length = 858
FEATURE                   Location/Qualifiers
source                    1..858
                          mol_type = protein
                          organism = synthetic construct
SEQUENCE: 5
MNIAPVKNLL NDQLPNFIKQ GYLFMSHQRR KAGVPADSNC PVTFPVLGGR ATLIRGEEAV  60
DFFYDESKIS RNGAMPTAIQ GPLFGDGAVH TLDGQAHKVR KSAMAAMAYD DERVEAFRGF  120
VEEEMKALIE RWKTNPGNIY DDVAVAYGRA AFRWAGVPAS DRELNKRATQ MSHLLDTFGE  180
VKQNVLSWMD RRKLDAWAED LIKKVRSGEL TVDPDSVVRH MADLRDEKGE LVTAKLAGIE  240
LQNLTRPTVA VSRFAAFAAV AMVENPEWAA KVKNAVEDAD GRLVNIPEAV AFAQETRRKY  300
PFVPMLPAMV KEDTELSGCP IQKGQRVFLD VLGTNNSPQL WNNPGEFNPQ RFLDTPDYES  360
IKGFIPQGGG DVLTGHRCPG EKIAVAALSS TVAALSADNV TISQETEDTT FSMTQLLTRP  420
RTGVRVTVSH SSGLVPRGSH MSDITVTNWA GNITYTAKEL LRPHSLDALR ALVADSARVR  480
VLGSGHSFNE IAEPGDGGVL LSLAGLPSVV DVDTAARTVR VGGGVRYAEL ARVVHARGLA  540
LPNMASLPHI SVAGSVATGT HGSGVGNGSL ASVVREVELV TADGSTVVIA RGDERFGGAV  600
TSLGALGVVT SLTLDLEPAY EMEQHVFTEL PLAGLDPATF ETVMAAAYSV SLFTDWRAPG  660
FRQVWLKRRT DRPLDGFPYA APAAEKMHPV PGMPAVNCTE QFGVPGPWHE RLPHFRAEFT  720
PSSGAELQSE YLMPREHALA ALHAMDAIRE TLAPVLQTCE IRTVAADAQW LSPAYGRDTV  780
AAHFTWVEDT AAVLPVVRRL EEALVPFAAR PHWGKVFTVP AGELRALYPR LADFGALAGA  840
LDPAGKFTNA FVRGVLAG                                               858

SEQ ID NO: 6              moltype = AA  length = 860
FEATURE                   Location/Qualifiers
source                    1..860
                          mol_type = protein
                          organism = synthetic construct
SEQUENCE: 6
MNIAPVKNLL NDQLPNFIKQ GYLFMSHQRR KAGVPADSNC PVTFPVLGGR ATLIRGEEAV  60
DFFYDESKIS RNGAMPTAIQ GPLFGDGAVH TLDGQAHKVR KSAMAAMAYD DERVEAFRGF  120
VEEEMKALIE RWKTNPGNIY DDVAVAYGRA AFRWAGVPAS DRELNKRATQ MSHLLDTFGE  180
VKQNVLSWMD RRKLDAWAED LIKKVRSGEL TVDPDSVVRH MADLRDEKGE LVTAKLAGIE  240
LQNLTRPTVA VSRFAAFAAV AMVENPEWAA KVKNAVEDAD GRLVNIPEAV AFAQETRRKY  300
PFVPMLPAMV KEDTELSGCP IQKGQRVFLD VLGTNNSPQL WNNPGEFNPQ RFLDTPDYES  360
IKGFIPQGGG DVLTGHRCPG EKIAVAALSS TVAALSADNV TISQETEDTT FSMTQLLTRP  420
RTGVRVTGSD ASAREATAKG SHMSDITVTN WAGNITYTAK ELLRPHSLDA LRALVADSAR  480
VRVLGSGHSF NEIAEPGDGG VLLSLAGLPS VVDVDTAART VRVGGGVRYA ELARVVHARG  540
LALPNMASLP HISVAGSVAT GTHGSGVGNG SLASVVREVE LVTADGSTVV IARGDERFGG  600
AVTSLGALGV VTSLTLDLEP AYEMEQHVFT ELPLAGLDPA TFETVMAAAY SVSLFTDWRA  660
PGFRQVWLKR RTDRPLDGFP YAAPAAEKMH PVPGMPAVNC TEQFGVPGPW HERLPHFRAE  720
FTPSSGAELQ SEYLMPREHA LAALHAMDAI RETLAPVLQT CEIRTVAADA QWLSPAYGRD  780
TVAAHFTWVE DTAAVLPVVR RLEEALVPFA ARPHWGKVFT VPAGELRALY PRLADFGALA  840
GALDPAGKFT NAFVRGVLAG                                             860

SEQ ID NO: 7              moltype = DNA  length = 2574
FEATURE                   Location/Qualifiers
source                    1..2574
                          mol_type = other DNA
                          organism = synthetic construct
SEQUENCE: 7
atgaacatcg cacccgtaaa aaatcttttg aatgaccagc tgcccaattt cattaagcag  60
ggctaccttt ttatgtccca ccagcgccgt aaggccgggg ttcccgcaga ttccaactgc  120
cccgttacct tccccgtcct gggaggaagg gccaccctaa ttcgaggtga agaggccgta  180
gatttcttct acgatgagtc taaaattagc cgtaacggtg ctatgcccac cgccattcag  240
gggccgctct ttggcgacgg tgccgtgcac accctcgacg gtcaggcgca taaggttcgt  300
aagtctgcca tggctgccat ggcctatgac gacgagcggg tagaggcttt caggggcttc  360
gtcgaagaag aaatgaaggc cctcattgag cggtggaaga ccaaccccgg caacatctac  420
gatgacgttg ctgtggccta cggtcgcgct gccttccgct gggccggggt gccagcctcc  480
gaccgcgaac tcaacaagcg agccacccag atgagccacc tgctcgacac gttcggcgag  540
gtcaagcaga acgtgctctc ctggatggac cgccgcaaac tcgatgcctg ggccgaagac  600
ctcatcaaaa aggtacgctc gggcgaactc acggttgacc ctgactctgt ggtgcgccac  660
atggcagatt tgcgtgatga gaagggcgaa ctggtcaccg ccaagctggc cggtatcgaa  720
ttgcagaacc tgactcgccc taccgtggcg gtctcccgct ttgcagcctt cgcagctgta  780
gccatggtcg aaaaccccga gtgggccgcc aaggtcaaga atgctgttga ggacgccgac  840
ggccgcctag tcaatatccc cgaagctgtt gccttcgccc aggagacccg ccgcaagtac  900
cccttcgtcc ccatgcttcc cgctatggtt aaggaagata ctgaactttc gggttgcccg  960
attcagaagg gccagcgggt gttccttgat gttttaggta caaacaactc accccaactc  1020
tggaacaacc ccggtgaatt caacccccag cgtttcttgg ataccccgga ctatgagtcc  1080
attaagggtt tcatccctca gggcggcgga gacgtgctca ccggccaccg ttgccccggc  1140
gagaagattg ctgtggcggc tctgtcttca accgttgcag cgctttcagc tgataacgtc  1200
accatctctc aagaaaccga agacaccact ttcagtatga cccagctact cacccgcccc  1260
aggacgggcg tacgcgtaac agtcagccac agcagcggcc tggtgccgcg cggcagccat  1320
atgtctgaca tcaccgttac caactgggct ggtaacatca cctacaccgc taaagaactg  1380
ctgcgtccgc actctctgga cgctctgcgt gctctggttg ctgactctgc tcgtgttcgt  1440
gttctgggtt ctggtcactc tttcaacgaa atcgctgaac cgggtgacgg tggtgttctg  1500
```

-continued

```
ctgtctctgg ctggtctgcc gtctgttgtt gacgttgaca ccgctgctcg taccgttcgt  1560
gttggtggtg gtgttcgtta cgctgaactg gctcgtgttg ttcacgctcg tggtctggct  1620
ctgccgaaca tggcttctct gccgcacatc tctgttgctg gttctgttgc taccggtacc  1680
cacggttctg gtgttggtaa cggttctctg gcttctgttg ttcgtgaagt tgaactggtt  1740
accgctgacg gttctaccgt tgttatcgct cgtggtgacg aacgtttcgg tggtgctgtt  1800
acctctctgg gtgctctggg tgttgttacc tctctgaccc tggacctgga accggcttac  1860
gaaatggaac agcacgtttt caccgaactg ccgctggctg gtctggaccc ggctaccttc  1920
gaaaccgtta tggctgctgc ttactctgtt tctctgttca ccgactggcg tgctccgggt  1980
ttccgtcagg tttggctgaa acgtcgtacc gaccgtccgc tggacggttt cccgtacgct  2040
gctccggctg ctgaaaaaat gcacccggtt ccgggtatgc cggctgttaa ctgcaccgaa  2100
cagttcggtg ttccgggtcc gtggcacgaa cgtctgccgc acttccgtgc tgaattcacc  2160
ccgtcttctg gtgctgaact gcagtctgaa tacctgatgc cgcgtgaaca cgctctggct  2220
gctctgcacg ctatggacgc tatccgtgaa accctggctc cggttctgca gacctgcgaa  2280
atccgtaccg ttgctgctga cgctcagtgg ctgtctccgg cttacggtcg tgacaccgtt  2340
gctgctcact tcacctgggt tgaagacacc gctgctgttc tgccggttgt tcgtcgtctg  2400
gaagaagctc tggttccgtt cgctgctcgt ccgcactggg gtaaagtttt caccgttccg  2460
gctggtgaac tgcgtgctct gtacccgcgt ctggctgact tcggtgctct ggctggtgct  2520
ctggacccgg ctggtaaatt caccaacgct ttcgttcgtg gtgttctggc tggt        2574

SEQ ID NO: 8           moltype = DNA  length = 2580
FEATURE                Location/Qualifiers
source                 1..2580
                       mol_type = other DNA
                       organism = synthetic construct
SEQUENCE: 8
atgaacatcg cacccgtaaa aaatcttttg aatgaccagc tgcccaattt cattaagcag  60
ggctaccttt ttatgtccca ccagcgccgt aaggccgggg ttcccgcaga ttccaactgc  120
cccgttacct tccccgtcct gggaggaagg gccaccctaa ttcgaggtga agaggccgta  180
gatttcttct acgatgagtc taaaattagc cgtaacggtg ctatgcccac cgccattcag  240
gggccgctct ttggcgacgg tgccgtgcac accctcgacg gtcaggcgca taaggttcgt  300
aagtctgcca tggctgccat ggcctatgac gacgagcggg tagaggcttt caggggcttc  360
gtcgaagaag aaatgaaggc cctcattgag cggtggaaga ccaaccccgg caacatctac  420
gatgacgttg ctgtggccta cggtcgcgct gccttccgct gggccggggt gccagcctcc  480
gaccgcgaac tcaacaagcg agccacccag atgagccacc tgctcgacac gttcggcgag  540
gtcaagcaga acgtgctctc ctggatggac cgccgcaaac tcgatgcctg ggccgaagac  600
ctcatcaaaa aggtacgctc gggcgaactc acggttgacc ctgactctgt ggtgcgccac  660
atggcagatt tgcgtgatga gaagggcgaa ctggtcaccg ccaagctggc cggtatcgaa  720
ttgcagaacc tgactcgccc taccgtggcg gtctcccgct ttgcagcctt cgcagctgta  780
gccatggtcg aaaaccccga gtgggccgcc aaggtcaaga atgctgttga ggacgccgac  840
ggccgcctag tcaatatccc cgaagctgtt gccttcgccc aggagacccg ccgcaagtac  900
cccttcgtcc ccatgcttcc cgctatggtt aaggaagata ctgaactttc gggttgcccg  960
attcagaagg gccagcgggt gttccttgat gttttaggta caaacaactc accccaactc  1020
tggaacaacc ccggtgaatt caacccccag cgtttcttgg ataccccgga ctatgagtcc  1080
attaagggtt tcatccctca gggcggcgga gacgtgctca ccggccaccg ttgccccggc  1140
gagaagattg ctgtggcggc tctgtcttca accgttgcag cgctttcagc tgataacgtc  1200
accatctctc aagaaaccga agacaccact ttcagtatga cccagctact cacccgcccc  1260
aggacgggcg tacgcgtaac aggcagcgac gcttctgctc gtgaagctac cgctaaaggc  1320
agccatatgt ctgacatcac cgttaccaac tgggctggta acatcaccta caccgctaaa  1380
gaactgctgc gtccgcactc tctggacgct ctgcgtgctc tggttgctga ctctgctcgt  1440
gttcgtgttc tgggttctgg tcactctttc aacgaaatcg ctgaaccggg tgacggtggt  1500
gttctgctgt ctctggctgg tctgccgtct gttgttgacg ttgacaccgc tgctcgtacc  1560
gttcgtgttg gtggtggtgt tcgttacgct gaactggctc gtgttgttca cgctcgtggt  1620
ctggctctgc cgaacatggc ttctctgccg cacatctctg ttgctggttc tgttgctacc  1680
ggtacccacg gttctggtgt tggtaacggt tctctggctt ctgttgttcg tgaagttgaa  1740
ctggttaccg ctgacggttc taccgttgtt atcgctcgtg gtgacgaacg tttcggtggt  1800
gctgttacct ctctgggtgc tctgggtgtt gttacctctc tgaccctgga cctggaaccg  1860
gcttacgaaa tggaacagca cgttttcacc gaactgccgc tggctggtct ggacccggct  1920
accttcgaaa ccgttatggc tgctgcttac tctgtttctc tgttcaccga ctggcgtgct  1980
ccgggtttcc gtcaggtttg gctgaaacgt cgtaccgacc gtccgctgga cggtttcccg  2040
tacgctgctc cggctgctga aaaaatgcac ccggttccgg gtatgccggc tgttaactgc  2100
accgaacagt tcggtgttcc gggtccgtgg cacgaacgtc tgccgcactt ccgtgctgaa  2160
ttcaccccgt cttctggtgc tgaactgcag tctgaatacc tgatgccgcg tgaacacgct  2220
ctggctgctc tgcacgctat ggacgctatc cgtgaaaccc tggctccggt tctgcagacc  2280
tgcgaaatcc gtaccgttgc tgctgacgct cagtggctgt ctccggctta cggtcgtgac  2340
accgttgctg ctcacttcac ctgggttgaa gacaccgctg ctgttctgcc ggttgttcgt  2400
cgtctggaag aagctctggt tccgttcgct gctcgtccgc actggggtaa agttttcacc  2460
gttccggctg gtgaactgcg tgctctgtac ccgcgtctgg ctgacttcgg tgctctggct  2520
ggtgctctgg acccggctgg taaattcacc aacgctttcg ttcgtggtgt tctggctggt  2580
```

CHIMERIC ENZYME AND METHOD FOR PRODUCING TERMINAL ALKENES

TECHNICAL FIELD

The present invention concerns a chimeric enzyme constructed for the production of terminal alkenes from fatty acids, as well as the process for the production of said alkenes using said enzyme. The present invention belongs to the field of industrial biotechnology and has application in the biofuels and renewable chemicals industry.

BACKGROUND AND PRIOR ART

Terminal alkenes, or alpha olefins, are chemical compounds that can be synthesized from fatty acids of renewable origin. These molecules make up a relevant platform for the industrial production of polymers, fertilizers, lubricants, surfactants, biofuels and other compounds currently obtained via petrochemical routes, and the market size for them is projected at USD 13,464 million for 2022.

Given the relevance of these compounds for the chemical and biofuels industry, efforts to develop processes for producing terminal alkenes have been employed. Among the currently existing technologies for producing these molecules from fatty acids, the chemical route is one of the possibilities, but this is dependent on high temperature, high pressure and catalysis by heavy metals, which are harmful to the environment. Alternatively, the conversion of fatty acids into terminal alkenes can be carried out via a biotechnological route, using milder and more sustainable conditions. This route becomes especially interesting given the discussion about the need for responsible economic development, associated with environmental preservation. It is hoped that processes carried out in an environmentally sustainable way, with the use of materials and inputs from renewable sources or that make use of waste from other processes, become increasingly present on the world stage, contributing to the realization of the concept of Circular Economy.

Thus, within the scope of the biotechnological route for the production of terminal alkenes, scientific literature reports that the decarboxylase/peroxygenase enzyme called OleTJE, belonging to family 152 of the P450 superclass, has a unique property of removing oxygen from long-chain fatty acids. (C12-C20), generating 1-alkene as product. However, it is a very unstable enzyme, which is difficult to produce and requires high concentrations of salts (NaCl or KCl) for the decarboxylation reaction, which poses bottlenecks for its industrial use.

As well as OleTJE, there are enzymes from microorganisms such as *Kokuria rhizophila, Corynebacterium efficiens, Bacillus subtilis, Jeotgalicoccus* sp., *Staphylococcus massiliensis, Alicyclobacillus acidocaldarius* and other species, also with reported ability to convert fatty acids to terminal alkenes. However, a point to take into consideration is that, in general, the enzymatic route of fatty acids decarboxylation is dependent on hydrogen peroxide as a cofactor. The addition of peroxides to the reaction medium on an industrial scale imposes a cost and the need for an automatic injection mechanism at predetermined times.

A possible way to overcome the need to add hydrogen peroxide throughout the process is to generate it in situ for consumption during the conversion reaction. In this sense, CN107201356 (QINGDAO INSTITUTE OF BIOENERGY & BIOPROCESS TECHNOLOGY CAS BOEING INVESTMENT) presents, as a solution, the addition of a ferredoxin-ferredoxin reductase system to support the activity of the OleTJE enzyme. Similarly, CN112111477 (YANGZHOU UNIVERSITY) proposes the use of a glucose-glucose oxidase system for the generation of hydrogen peroxide, in a mild and controlled manner, to support an engineered enzyme (P450BS) in the conversion of fatty acids to alkenes. A similar proposal can also be found in EP1940348 (DUPONT NUTRITION BIOSCIENCES), which presents a composition comprising a system of coupled enzymes in which oxidoreductases generate hydrogen peroxide from sugars in the reaction medium for consumption by a decarboxylase enzyme.

It should be noted that, despite providing an alternative to the direct and controlled addition of hydrogen peroxide to the process, the solutions existing in the prior art impose an increase in the number of reagents necessary to carry out the conversion and require control so that both enzymes (peroxide generator and decarboxylase) are active under the reaction conditions. It is always interesting and preferable for a process to have few steps, ease of control and operation. Another point to note is that the coupling of an in situ peroxide generation system requires its own substrate for this reaction to take place. As described, the solutions proposed in the prior art employ ferredoxin or glucose/sugars as substrates, but one possibility of making the in situ peroxide generation process even more sustainable, adhering to the concept of circular economy, would be to carry out this reaction from waste from other processes.

Within this context, an extremely relevant waste in the current scenario is glycerol. In the production of biofuels alone, it is estimated that for every 1000 kilos of product such as bioethanol and biodiesel, 100 kilos of glycerol are generated. It is important to highlight that other important industries, such as oleochemistry, for example, also generate glycerol as a process residue. The volume of glycerol currently generated is greater than the capacity that the market can absorb. As a result, this waste has a low added value and, as an aggravating factor, the unused glycerol is destined for burning: in addition to the environmental problems inherent to the burning of compounds in general, the partial burning of glycerol generates acrolein, a molecule with carcinogenic potential. The conversion of glycerol through biotechnological processes into products with higher added value is a relevant alternative for reducing these problems.

Given this information, there are gaps to be filled and improved, aiming to make the biotechnological route of converting fatty acids to terminal alkenes even more practical and industrially attractive.

SUMMARY OF THE INVENTION

As a way of solving the bottlenecks presented, the present invention is, in a first aspect, a chimeric enzyme constructed for the production of terminal alkenes from fatty acids. The chimeric enzyme of the present invention is the combination of a decarboxylase enzyme, which converts fatty acids to terminal alkenes, with a peroxide-generating enzyme, a cofactor of the reaction, by means of a linker sequence. The main advantage of the chimeric enzyme of the present invention is the fact that it has both functions necessary for the reaction in a single product, bringing economy and ease to the process. Furthermore, the enzyme of the present invention is capable of producing hydrogen peroxide in situ from glycerol, which favors a more sustainable industry, within the concept of circular economy, by allocating part of what would be disintegrated by burning to an application with greater added value. Furthermore, the chimeric enzyme of the present invention does not require salt-saturated media to carry out the conversion of fatty acids to alkenes.

It is worth noting that not every enzyme with any similarity to the one proposed in this invention will be capable of application in an industrial process as it does not have stability in the soluble form, a fundamental characteristic presented by the chimeric enzyme of the present invention. Furthermore, the joining of two or more sequences can result in a non-functional product or one that performs below expectations.

In this sense, given the aforementioned, the present invention is, in a second aspect, a process for producing alkenes from fatty acids using the chimeric enzyme referred to in this invention. As an advantage, the process of the present invention exhibits a similar performance to that of the conventional process, which involves the isolated decarboxylase enzyme and the direct addition of hydrogen peroxide to the medium, starting from low concentrations of the enzyme of the present invention, which reinforces that the sequences claimed below are functional and present an advance in relation to the prior art. Furthermore, the process provides an alternative destination to burning glycerol, using it to produce compounds with high added value and reducing the environmental impacts caused by the current management of this waste.

DETAILED DESCRIPTION OF THE INVENTION

Figure 1:
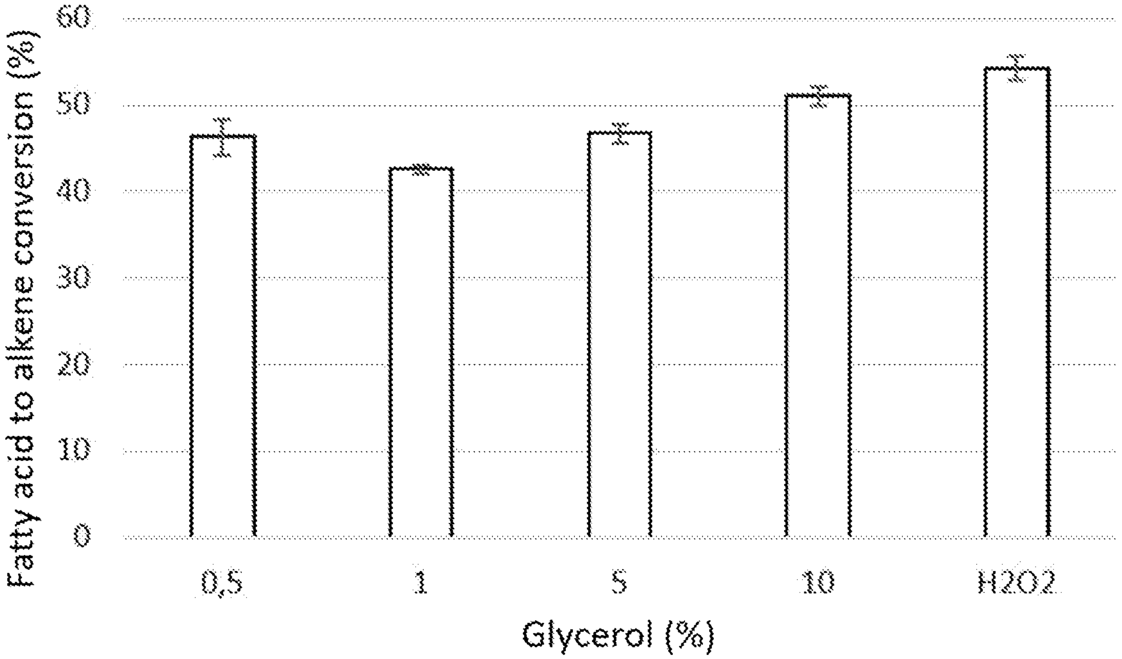
FIG. 1 graphically presents the percentage of conversion of myristic acid (C14:0) to its corresponding terminal alkene (1-tridecene) by means of the chimeric enzyme of the present invention, using said enzyme with flexible linking sequence (SEQ ID NO: 3) at 1 μM, 0.5 mM myristic acid and concentrations between 0.5 and 10% of glycerol in the reaction medium (50 mM sodium phosphate buffer, pH 7.5). The reaction was carried out at 37° C. with slow stirring (300 rpm) for 30 min. Comparatively, the result of the conversion obtained using the decarboxylase enzyme (SEQ ID NO: 1) in the presence of hydrogen peroxide added to the medium (1 mM) is presented.

As previously stated, the present invention concerns a chimeric enzyme constructed for the production of terminal alkenes from fatty acids, as well as the process for the production of said alkenes using said enzyme. From this point onwards, aspects of the present invention are detailed.

The chimeric enzyme for the production of terminal alkenes of the present invention is characterized, firstly, by the fact that it performs the conversion of fatty acids using glycerol as a substrate for the in situ production of hydrogen peroxide.

The chimeric enzyme for the production of terminal alkenes of the present invention is characterized by comprising the decarboxylase enzyme SEQ ID NO: 1 linked in its terminal portion to the beginning of the alditol oxidase enzyme SEQ ID NO: 2, hydrogen peroxide generating enzyme, by means of a linker sequence. Said binding sequence is preferably selected from the group comprising SEQ ID NO: 3 and SEQ ID NO: 4.

Thus, an object of the present invention is a chimeric enzyme for the production of terminal alkenes characterized by having SEQ ID NO: 5, which is the decarboxylase enzyme SEQ ID NO: 1, linked in its terminal portion to the SEQ ID binding sequence NO: 3, in turn linked to the initial portion of the alditol oxidase enzyme SEQ ID NO: 2.

Also an object of the present invention is a chimeric enzyme for the production of terminal alkenes characterized by having SEQ ID NO: 6, which is the decarboxylase enzyme SEQ ID NO: 1, linked in its terminal portion to the binding sequence SEQ ID NO: 4, in turn linked to the initial portion of the enzyme alditol oxidase SEQ ID NO: 2.

The chimeric enzyme of the present invention has application in the conversion of fatty acids to alkenes. Therefore, a process for producing terminal alkenes is also an object of the present invention.

The process of the present invention is characterized by comprising the steps of: a) Contacting chimeric enzyme with a fatty acid in the presence of glycerol, forming a reaction medium; b) Keeping the reaction medium under heating and stirring for a period of time; and, c) Collecting the product.

In step a), the chimeric enzyme to be used is the decarboxylase SEQ ID NO: 1 joined in its terminal portion to the beginning of the alditol oxidase SEQ ID NO: 2 by means of a linker sequence. Said binding sequence is preferably selected from the group comprising SEQ ID NO: 3 and SEQ ID NO: 4. More specifically, the chimeric enzyme to be employed in step a) can be selected from the group comprising SEQ ID NO: 5 and SEQ ID NO: 6.

The fatty acid may be selected from the group comprising capric acid (C10:0), lauric acid (C12:0), myristic acid (C14:0), palmitic acid (C16:0), stearic acid (C18:0), oleic acid (C18:1) or combinations thereof.

Furthermore, the preferred ratio of chimeric enzyme to fatty acid in the medium is 1.0 μMol $L^{-1}$ of enzyme for 0.5 mMol $L^{-1}$ of fatty acid. Glycerol can be in concentrations preferably between 0.5 and 10% in the reaction medium.

In step b), the reaction medium must be heated to a temperature between 30 and 40° C., preferably 37° C.

The agitation imposed on the reaction medium at this stage of the process must be mild, up to 500 rpm, preferably 300 rpm.

The pH of the reaction medium must be maintained between 7.0 and 8.0, preferably 7.5.

Finally, the reaction medium must be maintained under the conditions set out for, preferably, 30 minutes.

In step c), the collected product can optionally be purified. For such a step, any separation and purification techniques known to one skilled in the art may be employed.

Below, as a basis, but without being restricted to them, examples of embodiments of the present invention are presented.

Example 1: Chimeric Enzyme Expression Procedure

The coding regions of the enzymes of the present invention (SEQ ID NO: 7 and SEQ ID NO: 8) were cloned individually into pET28a expression vectors, with a 6xHisTag tail to facilitate product purification. The recombinant vectors were transformed into *E. coli* BL21, and the expression of each of the chimeric enzymes was conducted in "Terrific Broth" (TB) medium. For expression, transformed bacteria were grown in 1 L of TB medium, at 30° C., containing the appropriate antibiotics. Upon reaching an optical density value equal to 1, the medium temperature was reduced to 18° C. and the induction of expression of the enzymes of the present invention was initiated with 0.2 mMol $L^{-1}$ de IPTG, 20 μMol $L^{-1}$ of hemin in 100 μMol $L^{-1}$ of 5-aminolevulinate. After 24 h of induction, the cells were isolated and used to purify the chimeric enzymes. Purification was carried out on nickel resin, with 25 mMol $L^{-1}$ sodium phosphate buffer (pH 7.5) and 500 mMol $L^{-1}$ NaCl. Chimeric enzymes were recovered on an imidazole gradient, from 0-500 mMol $L^{-1}$. Both constructions resulted in the production of soluble and functional chimeric enzymes (SEQ ID NO: 5 and SEQ ID NO: 6).

Example 2: Terminal Alkene Production Assay with Chimeric Enzymes

Conversion reactions of myristic acid to its corresponding terminal alkene (1-tridecene) were carried out with the chimeric enzymes separately, using a final volume of 1 mL. In all cases, the reaction medium was composed of the chimeric enzyme to be tested, at a concentration of 1 μMol $L^{-1}$, the fatty acid, at a concentration of 0.5 mMol $L^{-1}$, and 50 mM sodium phosphate buffer, pH 7.5. Different concentrations of glycerol (0.5, 1, 5 or 10%) were added to each reaction to evaluate the conversion rate (%) of myristic acid into 1-tridecene. All reactions were carried out at 37° C., with gentle stirring (300 rpm), for 30 min.

For comparison, a reaction with the traditional process of converting fatty acids to alkenes was carried out using the same process conditions, but replacing the chimeric enzymes with decarboxylase SEQ ID NO: 1 and glycerol with hydrogen peroxide at the concentration of 1 mM (final).

Figure 2:
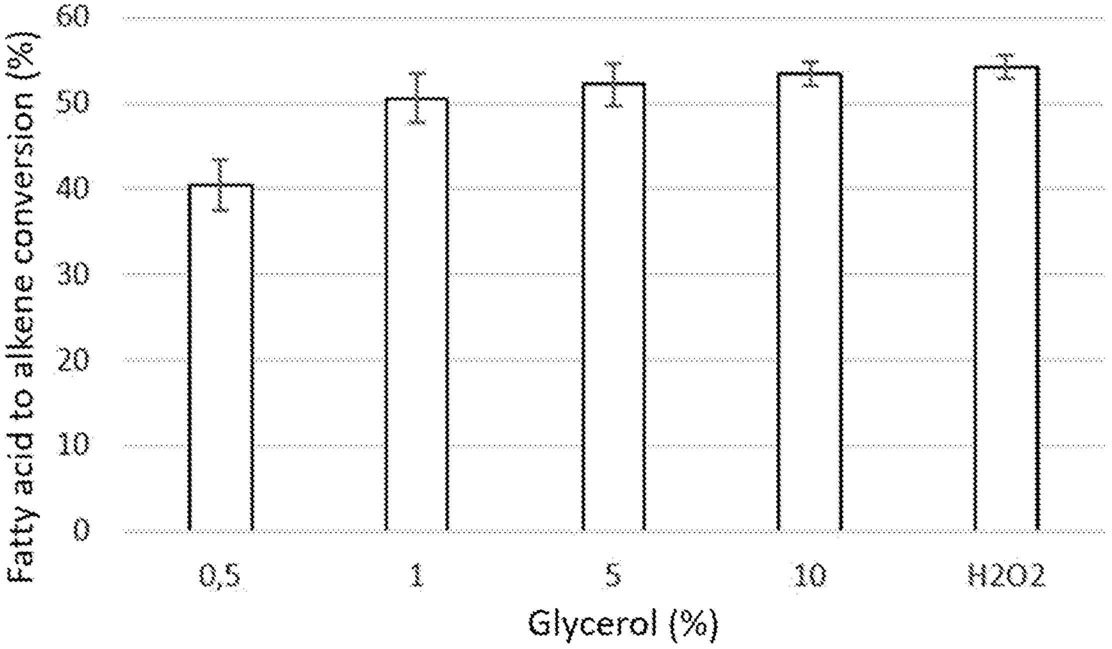
FIG. 2 graphically presents the percentage of conversion of myristic acid (C14:0) to its corresponding terminal alkene (1-tridecene) by means of the chimeric enzyme of the present invention, using said enzyme with a rigid binding sequence (SEQ ID NO: 4) at 1 μM, 0.5 mM myristic acid and concentrations between 0.5 and 10% of glycerol in the reaction medium (50 mM sodium phosphate buffer, pH 7.5). The reaction was carried out at 37° C. with slow stirring (300 rpm) for 30 min. Comparatively, the result of the conversion obtained using the decarboxylase enzyme (SEQ ID NO: 1) in the presence of hydrogen peroxide added to the medium (1 mM) is presented.

As a result, the traditional condition allowed a conversion of myristic acid to 1-tridecene of around 55% to be achieved. As can be seen in FIG. 1, the tests carried out with the chimeric enzyme SEQ ID NO: 5 of the present invention showed a conversion percentage between 40 and 50%, with the highest result being achieved with a concentration of 10% of glycerol. In FIG. 2, where the performance results of the chimeric enzyme SEQ ID NO: 6 are presented, a conversion between 40 and 55% can be seen, reaching these levels from 5% of glycerol in the reaction medium.

In this way, it is observed that the present invention makes it possible to generate peroxide in the reaction medium from glycerol. Instead of adding hydrogen peroxide to the medium, the addition of glycerol brings a new perspective to the disposal of this industrial waste in an effective way, using a single chimeric enzyme, without the need to use two enzyme systems to carry out the conversion reaction.

The invention claimed is:

1. A chimeric enzyme for the production of terminal alkenes characterized by comprising the decarboxylase enzyme of SEQ ID NO: 1 joined in its terminal portion to the beginning of the alditol oxidase enzyme of SEQ ID NO: 2 by means of a linker sequence.

2. The chimeric enzyme according to claim 1, characterized by the fact that the linker sequence is selected from the group comprising SEQ ID NO: 3 and SEQ ID NO: 4.

3. The chimeric enzyme according to claim 1, characterized by having the fusion protein of SEQ ID NO: 5.

4. The chimeric enzyme according to claim 1, characterized by having the fusion protein of SEQ ID NO: 6.

5. A process for the production of terminal alkenes characterized by comprising the steps of:

a) Contacting the chimeric enzyme of claim 1 with a fatty acid in the presence of glycerol, forming a reaction medium;

b) Keeping the reaction medium under heating and stirring for a period of time; and c) Collecting the product.

6. The process according to claim 5, characterized by the fact that the chimeric enzyme is the decarboxylase of SEQ ID NO: 1 linked in its terminal portion to the beginning of the alditol oxidase of SEQ ID NO: 2 by means of a linker sequence.

7. The process according to claim 6, characterized by the fact that the linker sequence is selected from the group comprising SEQ ID NO: 3 and SEQ ID NO: 4.

8. The process according to claim 5, characterized by the fact that the enzyme is selected from the group comprising SEQ ID NO: 5 and SEQ ID NO: 6.

9. The process according to claim 5, characterized by the fact that the fatty acid is selected from the group comprising capric acid (C10:0), lauric acid (C12:0), myristic acid (C14:0), palmitic acid (C16:0), stearic acid (C18:0), oleic acid (C18:0) or combinations thereof.

10. The process according to claim 5, characterized by the fact that the ratio between chimeric enzyme and fatty acid in the medium is 1.0 μMol $L^{-1}$ of enzyme for 0.5 mMol $L^{-1}$ of fatty acid.

11. The process according to claim 5, characterized by the fact that the concentration of glycerol in the medium is, between 0.5 and 10%.

12. The process according to claim 5, characterized by the fact that the reaction medium must be heated to a temperature between 30 and 40° C.

13. The process according to claim 5, characterized by the fact that agitation imposed on the medium is between 500 rpm to 300 rpm.

14. The process according to claim 5, characterized by the fact that the pH of the reaction medium is maintained between 7.0 and 8.0.

15. The process according to claim 5, characterized by the fact that the time is, 30 minutes.

* * * * *